US00PP10321P

United States Patent [19]

Kientzler

[11] Patent Number: Plant 10,321

[45] Date of Patent: Apr. 7, 1998

[54] NEW GUINEA IMPATIENS PLANT NAMED 'NEPTIS'

[75] Inventor: Ludwig Kientzler, Gensingen, Germany

[73] Assignee: Paul Ecke Ranch, Inc., Encinitas, Calif.

[21] Appl. No.: 778,172

[22] Filed: Jan. 2, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named 'Neptis', characterized by its flat and rounded red and pink bi-colored flowers; freely flowering habit; outwardly spreading, rounded and mounded growth habit; and medium green, glossy, non-variegated foliage.

1 Drawing Sheet

The present invention relates to a new and distinct cultivar of New Guinea Impatiens plant, botanically known as *Impatiens hawkeri*, known by the name Kinep, and hereinafter referred to by the cultivar name Neptis.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as N213 as the male, or pollen parent, with the proprietary seedling selection identified as Z661 as the female, or seed patent. The cultivar Neptis was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction. The following traits have been repeatedly observed and are determined to be the unique characteristics of 'Neptis'. These characteristics in combination distinguish 'Neptis' as a new and distinct cultivar: 1. Flat and rounded red and pink bi-colored flowers. 2. Freely flowering habit. 3. Outwardly spreading, rounded and mounded growth habit. 4. Medium green, glossy, non-variegated foliage.

The new New Guinea Impatiens is similar in flower color to the New Guinea Impatiens cultivar 'Celebration Cherry Star' (disclosed in U.S. Plant Pat. No. 8,407). However in side-by-side comparisons in Encinitas, Calif. under commercial practice, plants of the new New Guinea Impatiens differed from plants of the cultivar ('Guadeloupe' in the following characteristics:

1. Plants of the new New Guinea Impatiens are more outwardly spreading, mounded and rounded than plants of the cultivar 'Celebration Cherry Star'.

2. Plants of the new New Guinea Impatiens are more vigorous and taller and wider than plants of the cultivar ('Celebration Cherry Star'.

3. Plants of the new New Guinea Impatiens are more freely branching than plants of the cultivar 'Celebration Cherry Star'.

4. Leaves of plants of the new New Guinea Impatiens are larger than leaves of plants of the cultivar 'Celebration Cherry Star'.

5. Upper surfaces of leaves of plants of the new New Guinea Impatiens are lighter green than upper surfaces of leaves of plants of the cultivar 'Celebration Cherry Star'.

6. Flowers of plants of the new New Guinea Impatiens are positioned above the foliage whereas flowers of plants of the cultivar 'Celebration Cherry Star' are positioned slightly below the foliage.

A detailed comparison of plants of the new New Guinea Impatiens and the cultivar 'Celebration Cherry Star' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of 'Neptis'.

The second photograph comprises a close-up view of typical flowers and upper (left) and lower (right) surfaces of leaves of the cultivars 'Celebration Cherry Star' (top) and 'Neptis' (bottom of photo).

Flower and foliage colors in the photographs may differ from the actual colors due to light reflectance.

The cultivar Neptis has not been observed under all possible environmental conditions. The phenotype may vary somewhat with variations in environment such as temperature and light intensity, without, however, any variance in genotype. The following observations, measurements and comparisons describe plants grown 10-cm pots in Encinitas, Calif. under commercial practice in a fiberglass-covered greenhouse with day temperatures ranging from 23 to 29C. and night temperatures ranging from 16 to 18C. and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* 'Neptis'

*Commercial.*—New Guinea Impatiens cv. 'Neptis'.

Parentage:

*Male parent.*—Proprietary seedling selection N213.

*Female parent.*—Proprietary seedling selection Z661.

Propagation:

*Type cutting.*—Terminal cuttings.

*Time to initiate roots.*—About 15 days with 21C. soil temperature.

Plant Description:

*Plant form.*—Outwardly spreading, rounded and mounting.

*Growth habit.*—Moderately vigorous and moderate branching with dense and bushy growth. Suitable for 10 to 25-cm containers.

*Plant size.*—Height: About 17 cm. Width or spread: About 25 cm.

*Lateral branches.*—Quantity: Five to seven. Size: Length: About 18 cm. Diameter: About 6 mm. Internode length: About 7 cm. Color: Green with red, 59A, streaks.

*Foliage description.*—Leaves simple, generally symmetrical, abundant, opposite or in whorls of three, horizontal to plant and flat in aspect. Size, largest leaves: Length: About 13 cm. Width: About 6 cm. Shape: Ovate with acumenate apex, attenuate base and ciliate margin. Texture: Smooth, glossy. Color: Young foliage, upper surface: 144A with overtones of 59A. Young foliage, lower surface: 59A. Fully expanded foliage, upper surface: 137A. Fully expanded foliage, lower surface: 59A. Venation, upper surface: 59A. Venation, lower surface: 59A. Petiole: Size: Length: About 2.75 cm. Color: Diameter: About 4 mm.

Flower description:

*Flower type and habit.*—Red and pink bi-colored flowers. Freely and continuously flowering. Flowers arise from leaf axils. Usually ten flowers per lateral branch. Flowers positioned above the foliage and face upward or outward. Flowers flat and rounded. Flowers persistent.

*Flowering season.*—Year-round under greenhouse conditions. In the garden, flowering is continuous from spring until fall.

*Flower size.*—Length: About 6 cm. Width: About 6 cm. Depth: About 5 mm.

*Flower buds.*—Size: Length: About 1.6 cm. Diameter: About 1 cm. Shape: Ovoid. Color: 46A.

*Petals.*—Quantity: Five. Size (largest petals): Length: Top petal: About 2.75 cm. Middle petals: About 2.75 cm. Bottom petals: About 2.75 cm. Width: Top petal: About 5 cm. Middle petals: About 4 cm. Bottom petals: About 4.25 cm. Shape: Cordate with emarginate apex, cuneate or obtuse base and entire margin. Texture: Satiny, smooth. Color: When opening, upper surface: Iridescent, background of 62A/65A with streaks of 46B, centers of 45B, and 53A at base. When opening, lower surface: Iridescent, 46A/46B. Fully opened, upper surface: Iridescent, background of 62A/65A with streaks of 46B, centers of 45B, and 53A at base. Fully opened, lower surface: Iridescent, 46B/46C. Fading to: Petal colors do not fade.

*Spur.*—Length: About 5.5 cm. Shape: Narrow and curved. Color: Proximal: 46A. Distal: 144A.

*Peduncles.*—Length: About 4.5 cm. Angle: Erect and outward. Strength: Strong. Color: 144A.

*Reproductive organs.*—Androecium: Stamen number: Five, anthers fused, filaments free. Anther shape: Obovate. Anther size: 6 by 4 mm. Anther color: Very light yellow. Amount of pollen: Moderate. Pollen color: Light yellow/cream. Gynoecium: Five-loculate fused. Gynoecium color: 144A to 59A at maturity.

Disease resistance: Under commercial conditions, resistance nor susceptibility to pathogens has not been observed.

Seed development: Seed production is not usually observed.

CHART A

| CHARACTERISTIC | 'NEPTIS' | 'CELEBRATION CHERRY STAR' |
|---|---|---|
| GROWTH HABIT | Outwardly spreading, rounded and mounded | Upright and flat |
| PLANT HEIGHT | About 17 cm | About 13 cm |
| PLANT WIDTH | About 25 cm | About 16 cm |
| VIGOR | Moderate | Low |
| BRANCHING HABIT | Moderate, 5 to 7 lateral branches per plant | Low, 3 to 5 lateral branches per plant |
| LATERAL BRANCH LENGTH | About 18 cm | About 10 cm |
| INTERNODE LENGTH | About 7 cm | About 4 cm |
| LEAF LENGTH | About 13 cm | About 10 cm |
| LEAF WIDTH | About 6 cm | About 5 cm |
| LEAF COLOR, FULLY EXPANDED, UPPER SURFACE | 137A | Darker than 147A |
| PETIOLE LENGTH | About 2.75 cm | About 2,5 cm |
| PETIOLE DIAMETER | About 4 mm | About 3 mm |
| PETIOLE COLOR | 59A | Light green, 59A adaxial surface |
| QUANTITY OF FLOWERS PER LATERAL STEM | About 10 | About 9 |
| FLOWER POSITION | Above the foliage | Slightly below foliage |
| FLOWER SHAPE | Rounded | Rounded to star-shaped |
| PETAL COLOR, OPENED, UPPER SURFACE | 62A/65A background with 45B center and 53A at base | Lighter than 50B with 44B center and 57A at base |
| PETAL COLOR, OPENED, LOWER SURFACE | 46B/46C | 43C |
| FLOWER BUD COLOR | 46A | 44B |

It is claimed:

1. A new and distinct cultivar of New Guinea Impatiens plant named 'Neptis', as illustrated and described.

* * * * *

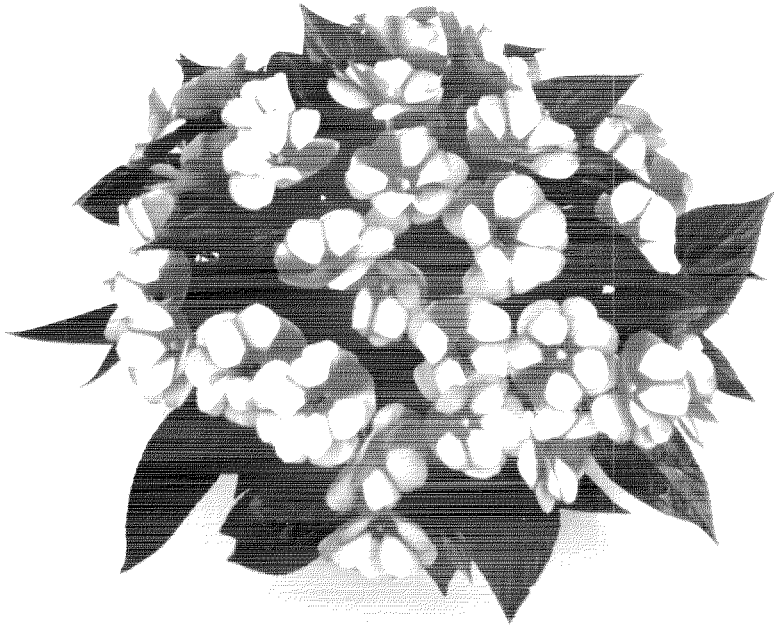
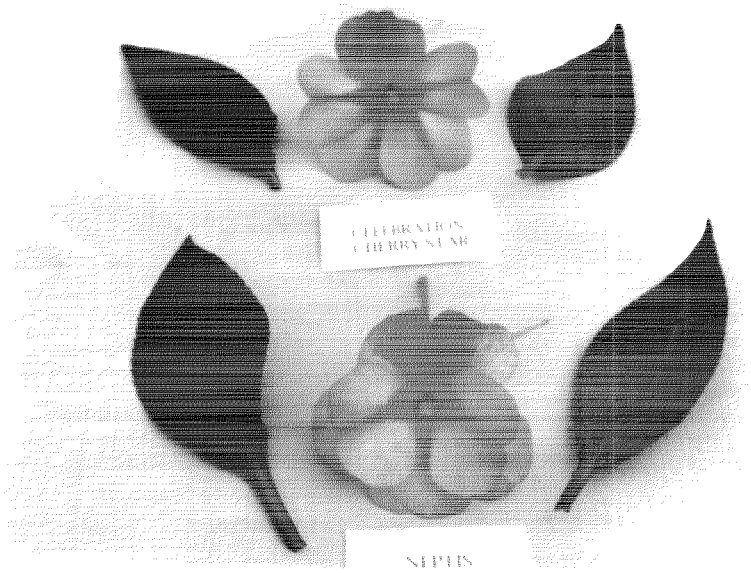
CELEBRATION
CHERRY SUAR
NEPTIS